(12) United States Patent
Schraga

(10) Patent No.: US 7,678,126 B2
(45) Date of Patent: Mar. 16, 2010

(54) LANCET DEPTH ADJUSTMENT ASSEMBLY

(76) Inventor: Steven Schraga, 2056 NE. 153 St., Surfside, FL (US) 33162

( * ) Notice: Subject to any disclaimer, the term of this patent is extended or adjusted under 35 U.S.C. 154(b) by 1099 days.

(21) Appl. No.: 11/121,312

(22) Filed: May 3, 2005

(65) Prior Publication Data
US 2005/0245955 A1    Nov. 3, 2005

Related U.S. Application Data

(63) Continuation-in-part of application No. 09/995,411, filed on Nov. 27, 2001, now Pat. No. 6,887,253, which is a continuation of application No. 09/477,950, filed on Jan. 5, 2000, now Pat. No. 6,322,575.

(51) Int. Cl.
*A61B 17/32* (2006.01)
(52) U.S. Cl. ..................................... 606/181
(58) Field of Classification Search ......... 606/181–189, 606/167; D24/147
See application file for complete search history.

(56) References Cited

U.S. PATENT DOCUMENTS

| | | | |
|---|---|---|---|
| 2,711,738 A | 6/1955 | Kelly et al. | |
| 3,483,810 A | 12/1969 | Peters et al. | |
| 3,906,626 A | 9/1975 | Riuli | |
| 4,373,526 A | 2/1983 | Kling | |
| 4,449,529 A | 5/1984 | Burns et al. | |
| 4,469,110 A | 9/1984 | Slama | |
| 4,535,769 A | 8/1985 | Burns | |
| 4,573,976 A | 3/1986 | Sampson et al. | |
| 4,610,620 A | 9/1986 | Gray | |
| 4,655,750 A | 4/1987 | Vaillancourt | |
| 4,735,202 A | 4/1988 | Williams | |
| 4,752,290 A | 6/1988 | Schramm | |
| 4,758,231 A | 7/1988 | Haber et al. | |
| 4,817,603 A | 4/1989 | Turner et al. | |
| 4,863,436 A | 9/1989 | Glick | |

(Continued)

FOREIGN PATENT DOCUMENTS

EP    0 293 092 A    11/1988

(Continued)

*Primary Examiner*—Cris L Rodriguez
*Assistant Examiner*—Heidi M Eide
(74) *Attorney, Agent, or Firm*—Malloy & Malloy, P.A.

(57) ABSTRACT

A lancet depth adjustment assembly structured to be used use with a lancet device of the type including a lancet disposed movably within a housing so as to pass into a piercing orientation wherein a piercing tip of the lancet protrudes from a piercing aperture defined in the housing. The lancet depth adjustment assembly includes a depth adjustment element movably secured in overlying relation to the piercing aperture of the housing and having a piercing access including one or more openings structured to permit passage of the piercing tip of the lancet therethrough. The depth adjustment element is structured to be interposed between a finger of a patient and the piercing aperture so as to define a spacing therebetween, and accordingly define a depth to which the piercing tip, which protrudes a defined amount from the housing, penetrates the body part. Furthermore, the depth adjustment element is constructed of a varying thickness so as to vary the spacing between the body part and the piercing aperture in accordance with a thickness of a portion of the depth adjustment element disposed in overlying relation to the piercing aperture at a time of operation of the lancet device.

15 Claims, 2 Drawing Sheets

U.S. PATENT DOCUMENTS

| | | | |
|---|---|---|---|
| 4,895,147 A | 1/1990 | Bodicky et al. |
| 4,897,083 A | 1/1990 | Martell |
| 4,908,023 A | 3/1990 | Yuen |
| 4,944,736 A | 7/1990 | Holtz |
| 4,994,045 A | 2/1991 | Ranford |
| 4,994,068 A | 2/1991 | Hufnagle |
| 5,024,660 A | 6/1991 | McNaughton |
| 5,026,388 A | 6/1991 | Ingalz |
| 5,057,079 A | 10/1991 | Tiemann et al. |
| 5,088,996 A | 2/1992 | Kopfer et al. |
| 5,116,351 A | 5/1992 | Frassetti |
| 5,147,326 A | 9/1992 | Talonn et al. |
| 5,147,375 A | 9/1992 | Sullivan et al. |
| 5,160,326 A | 11/1992 | Talonn et al. |
| 5,181,609 A | 1/1993 | Spielmann et al. |
| 5,207,696 A | 5/1993 | Matwijcow |
| 5,219,333 A | 6/1993 | Sagstetter et al. |
| 5,222,945 A | 6/1993 | Basnight |
| 5,224,950 A | 7/1993 | Prywes |
| 5,241,969 A | 9/1993 | Carson et al. |
| 5,247,972 A | 9/1993 | Tetreault |
| 5,250,026 A | 10/1993 | Ehrlich et al. |
| 5,250,063 A | 10/1993 | Abidin et al. |
| 5,279,581 A | 1/1994 | Firth et al. |
| 5,297,599 A | 3/1994 | Bucheli |
| 5,304,136 A | 4/1994 | Erskine et al. |
| 5,304,192 A | 4/1994 | Crouse |
| 5,312,347 A | 5/1994 | Osborne et al. |
| 5,312,365 A | 5/1994 | Firth et al. |
| 5,318,583 A | 6/1994 | Rabenau et al. |
| 5,318,584 A | 6/1994 | Lange et al. |
| 5,330,492 A | 7/1994 | Haugen |
| 5,336,199 A | 8/1994 | Castillo et al. |
| 5,346,480 A | 9/1994 | Hess et al. |
| 5,350,392 A | 9/1994 | Purcell et al. |
| 5,356,406 A | 10/1994 | Schraga |
| 5,356,420 A | 10/1994 | Czernecki et al. |
| 5,361,902 A | 11/1994 | Abidin et al. |
| 5,395,388 A * | 3/1995 | Schraga ............... 606/182 |
| 5,417,662 A | 5/1995 | Hjertman et al. |
| 5,423,847 A | 6/1995 | Strong et al. |
| 5,439,473 A | 8/1995 | Jorgensen |
| 5,454,828 A | 10/1995 | Schraga |
| 5,462,535 A | 10/1995 | Bonnichsen et al. |
| 5,464,418 A | 11/1995 | Schraga |
| 5,468,233 A | 11/1995 | Schraga |
| 5,469,964 A | 11/1995 | Bailey |
| 5,487,748 A | 1/1996 | Marshall et al. |
| 5,496,340 A | 3/1996 | Abidin et al. |
| 5,501,672 A | 3/1996 | Firth et al. |
| 5,518,004 A | 5/1996 | Schraga |
| 5,527,334 A | 6/1996 | Kanner et al. |
| 5,531,713 A | 7/1996 | Mastronardi et al. |
| D376,203 S | 12/1996 | Schraga |
| 5,584,846 A | 12/1996 | Mawhirt et al. |
| 5,599,323 A | 2/1997 | Bonnichsen et al. |
| 5,628,764 A | 5/1997 | Schraga |
| 5,628,765 A | 5/1997 | Morita |
| 5,643,306 A | 7/1997 | Schraga |
| 5,697,916 A | 12/1997 | Schraga |
| 5,706,942 A | 1/1998 | Vila et al. |
| 5,707,384 A | 1/1998 | Kim |
| 5,730,753 A | 3/1998 | Morita |
| 5,735,823 A | 4/1998 | Berger |
| 5,738,665 A | 4/1998 | Caizza et al. |
| 5,741,288 A | 4/1998 | Rife |
| 5,746,761 A | 5/1998 | Turchin |
| 5,755,733 A | 5/1998 | Morita |
| 5,772,636 A | 6/1998 | Brimhall et al. |
| 5,792,122 A | 8/1998 | Brimhall et al. |
| 5,797,940 A | 8/1998 | Mawhirt et al. |
| 5,797,942 A | 8/1998 | Schraga |
| 5,836,920 A | 11/1998 | Robertson |
| 5,868,771 A | 2/1999 | Herbert et al. |
| 5,871,494 A | 2/1999 | Simons et al. |
| 5,873,856 A | 2/1999 | Hjertman et al. |
| 5,891,103 A | 4/1999 | Burns |
| 5,908,434 A | 6/1999 | Schraga |
| 5,916,230 A * | 6/1999 | Brenneman et al. ......... 606/172 |
| 5,947,934 A | 9/1999 | Hansen et al. |
| 5,951,530 A | 9/1999 | Steengaard et al. |
| 5,951,582 A | 9/1999 | Thorne et al. |
| 5,954,738 A | 9/1999 | LeVaughn et al. |
| 5,968,021 A | 10/1999 | Ejlersen |
| 5,971,966 A | 10/1999 | Lav |
| 5,980,491 A | 11/1999 | Hansen |
| 5,984,906 A | 11/1999 | Bonnichsen et al. |
| 6,015,397 A | 1/2000 | Elson et al. |
| 6,022,366 A | 2/2000 | Schraga |
| 6,050,977 A | 4/2000 | Adams |
| 6,056,765 A | 5/2000 | Bajaj et al. |
| 6,074,372 A | 6/2000 | Hansen |
| 6,077,253 A | 6/2000 | Cosme |
| 6,110,149 A | 8/2000 | Klitgaard et al. |
| 6,149,608 A | 11/2000 | Marshall et al. |
| 6,156,051 A | 12/2000 | Schraga |
| 6,168,606 B1 | 1/2001 | Levin et al. |
| 6,190,398 B1 | 2/2001 | Schraga |
| 6,213,977 B1 | 4/2001 | Hjertman et al. |
| 6,216,868 B1 | 4/2001 | Rastegar et al. |
| 6,228,100 B1 | 5/2001 | Schraga |
| 6,248,120 B1 | 6/2001 | Wyszogrodzki |
| 6,258,112 B1 | 7/2001 | Schraga |
| 6,302,869 B1 | 10/2001 | Klitgaard |
| 6,322,574 B1 | 11/2001 | Lloyd et al. |
| 6,322,575 B1 | 11/2001 | Schraga |
| 6,346,114 B1 | 2/2002 | Schraga |
| 6,358,265 B1 | 3/2002 | Thorne, Jr. et al. |
| 6,514,270 B1 | 2/2003 | Schraga |
| 6,530,937 B1 | 3/2003 | Schraga |
| 6,764,496 B2 | 7/2004 | Schraga |
| 2002/0004649 A1 | 1/2002 | Jansen et al. |
| 2006/0184189 A1* | 8/2006 | Olson et al. ............... 606/181 |

FOREIGN PATENT DOCUMENTS

| | | |
|---|---|---|
| EP | 0 668 049 A1 | 8/1995 |
| EP | 0 894 471 A2 | 2/1999 |
| WO | WO 91/00215 | 1/1991 |
| WO | WO 95/16400 A1 | 6/1995 |
| WO | WO 00/78203 A2 | 12/2000 |
| WO | WO 00/78214 A1 | 12/2000 |
| WO | WO 01/32086 A1 | 10/2001 |

* cited by examiner

LANCET DEPTH ADJUSTMENT ASSEMBLY

CLAIM OF PRIORITY

The present is a continuation-in-part of U.S. patent application Ser. No. 09/995,411, filed Nov. 27, 2001, which is issuing as U.S. Pat. No. 6,887,253 on May 3, 2005, which is a continuation of U.S. patent application Ser. No. 09/477,950, filed Jan. 5, 2000, which is issuing as U.S. Pat. No. 6,322,575 on Nov. 27, 2001, the contents of which are hereby incorporated by reference.

BACKGROUND OF THE INVENTION

1. Field of the Invention

The present invention relates to a lancet depth adjustment assembly structured to be interposed between a body part to be pierced, such as a patient's finger or earlobe, and a piercing aperture of a lancet device housing, so as to effectively define and vary a depth to which a piercing tip of the lancet is able to penetrate the patient's body part disposed thereon. As such a patient can effectively select and define a sensitivity level that corresponds their particular needs and circumstance in a substantially easy to use manner which effectively maintains the finger properly positioned and is configured so as to be conveniently and cost effectively configured for utilization with a wide variety of existing lancet device designs.

2. Description of the Related Art

Lancet devices are commonly utilized devices which allow patients and medical practitioners to "prick" a patient's skin in order to effectively obtain a blood sample for a variety of tests. Typically these lancet devices involve the driving of a lancet tip into the patient's skin so as to result in bleeding by the patient, thereby allowing the sample to be gathered. Moreover, although these tests are often performed in a hospital or laboratory environment, because of the prevalence of many home testing kits, more and more, individual patients are turning to self testing, and as a result, independently utilize the lancet device so as to obtain their own blood sample.

Conventional lancet devices available in the art typically range from single use, disposable lancets, to re-useable lancet devices wherein an individual lancet can be removed and replaced after each use. Moreover, as a result of the increasing popularity of blood testing procedures, especially by individual patients, the field of art associated with lancet devices is quite crowded, with a variety of often complex and intricate structures being utilized to drive the piercing tip of the lancet into the flesh of a patent. In particular, the typical lancet device generally utilizes a disposable lancet, often of a standard dimension, contained in a housing for firing. As such, a variety of different, lancet devices have been provided, some providing for re-use through internal or external cocking of the firing mechanism and providing an actuation button on a side thereof for triggering of the piercing action.

Typically, most conventional lancet devices are constructed such that when fired the piercing tip of a particular lancet protrudes, at least temporarily, a defined amount from a piercing aperture of the housing. This amount or depth to which the piercing tip protrudes is traditionally a standard amount which is sufficiently effective to pierce the skin of most patients, thereby resulting in generation of the blood sample. Unfortunately, with some types of lancets, some patients and/or depending upon the circumstance, the standard depth which the piercing tip protrudes may not be ideal. For example, lancet devices typically are set to pierce a maximum depth which is acceptable to most individuals and may be necessary for some patients, such as those experiencing swelling, the formation of a callous, and/or who have normally thicker skin. Conversely, however, some patients, either at all times or at selective times depending upon their condition, are very sensitive and excessive penetration can lead to excessive bleeding and/or a substantially amount of pain. As a result, in such patients a standard, maximum depth is generally undesirable. Furthermore, it is also recognized that a wide spectrum of different lancet gauges are becoming increasingly available, with many companies turning to the manufacture of thinner gauge lancets which are necessarily longer. For example, a thicker gauge lancet does not have to penetrate as far to produce a sufficient sample, while thinner gauge lancets must penetrate further to produce a sufficient sample. Unfortunately, however, the increased penetration that results from the longer, thinner lancets, tends to be more painful and may therefore be excessive for some patients.

Accordingly, it would be highly beneficial to provide a depth adjustment assembly which is substantially accurate and easy to utilize, and which allows a patient to effectively vary a depth to which a piercing tip of the lancet would penetrate their skin. Furthermore, such a depth should be adjustable either a single time, for patients that have a requirement for a varied and specific depth on a permanent basis, or on a variable basis for patients who require different depths at different times. Indeed, such a configuration would be particularly beneficial if a common device needs to be utilized by many different patients, such as in a household with multiple diabetics, merely by replacing the used lancet with a new, sterile lancet. (Of course, such multi-patient use of a lancet device is never recommended.)

It would also be beneficial to provide such a depth adjustment assembly which is substantially effective and accurate, and is also cost effective and convenient to implement on a wide variety of existing lancet device configurations. For example, many individuals have particular preferences and/or needs with regard to the specific lancet devices that they utilize and/or have become accustomed to utilizing. As a result, it would be beneficial to provide a depth adjustment assembly which can be effectively configured for utilization with a majority of such lancet device designs, providing those designs with a beneficial degree adjustability, without affecting their normal mode of operation.

SUMMARY OF THE INVENTION

The present invention relates to a lancet depth adjustment assembly. In particular, the lancet depth adjustment assembly is structured to be used with a lancet device, preferably of the type that includes a lancet movably disposed within a housing and structured to at least temporarily move into a piercing orientation wherein a piercing tip of the lancet protrudes from a piercing aperture defined in the housing. Moreover, the lancet device is preferably of the type that protrudes through the piercing tip a predetermined, uniform amount, each time it is used.

Preferably, the lancet depth adjustment assembly includes a depth adjustment element. The depth adjustment element is preferably movably secured in at least partially and/or temporarily overlying relation to the piercing aperture of the housing. Of course, the piercing aperture of the housing may be of a finite size, and/or may comprise a completely open end of the housing, with the depth adjustment element being disposed operatively thereover.

The depth adjustment element further includes a piercing access. In particular, the piercing access includes one more openings and is structured to permit passage of the piercing tip of the lancet therethrough after it has passed through the piercing aperture of the housing. As such, the depth adjustment element is structured and disposed to be at least temporarily and at least partially interposed between a body part, such as the finger, of a patient and the piercing aperture during use of the lancet device.

The depth adjustment element is thereby structured to define a spacing between the patient's finger and the piercing aperture, and in turn define a depth to which the piercing tip can penetrate the finger. For example, as the piercing tip is generally configured to pass a predefined distance through the piercing aperture of the housing, a larger spacing between the finger and the piercing aperture, as defined by the depth adjustment element, reduces the depth to which the piercing tip ultimately penetrates the finger.

Although variable spacing is preferably provided by a single adjustable depth adjustment element, as will be described, if desired, interchangeable, different sized depth adjustment elements may be provided so as to vary the spacing. Preferably the depth adjustment element includes a varying thickness. In particular, the varying thickness is provided so as to vary a spacing between an exterior surface of the depth adjustment element and the piercing aperture. As a result, the spacing between the finger, which engages the exterior surface of the depth adjustment element, and the piercing aperture is also varied in accordance with a thickness of the portion of the depth adjustment element that is disposed in overlying relation to the piercing aperture when the lancet device is utilized.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
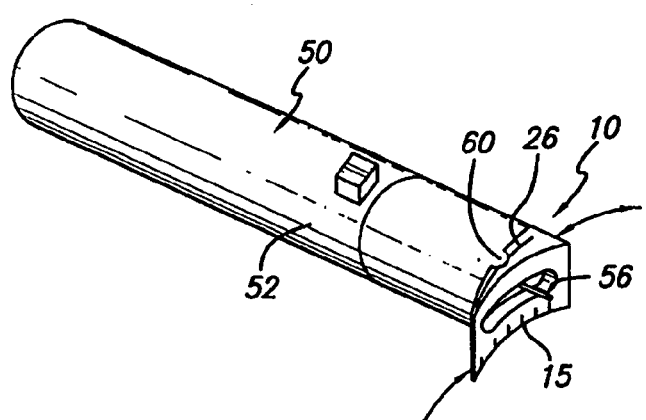
FIG. 1 is a perspective illustration of an embodiment of the depth adjustment assembly of the present invention operatively disposed on a lancet device.

Shown throughout the Figures, the present invention is directed towards a lancet depth adjustment assembly, generally indicated as 10. The depth adjustment assembly 10 is preferably structured for use in conjunction with a lancet device 50, that is normally used to fire a lancet into a patient's skin, such as at a patient's finger or earlobe, so as to allow a blood sample to be generated and collected. (Although the present invention can be used when piercing any portion of a patient's body, for purposes of clarity only, the following description is made primarily with reference to the piercing of a finger.) Although, there are a variety of different types and configurations of lancet devices 50 which may be utilized with the lancet depth adjustment assembly 10 of the present invention, preferably the lancet device 50 is of the type which includes a housing 52 that contains a lancet with a piercing tip 56 movably disposed therein. Moreover, the lancet device 50 is also preferably configured such that the lancet is at least temporarily movable into a piercing orientation wherein the piercing tip 56 of a lancet protrudes through a piercing aperture 54 defined in the housing 52. Of course, the piercing aperture 54 is generally small and sized to receive merely the piercing tip 56 of the lancet therethrough, however, it is also understood that alternatively the piercing aperture may be much larger, including a completely open end of the housing 52. In such an alternate embodiment, at least part of the structure of the depth adjustment assembly 10, to be described, can generally define and/or enclose the end of the housing 52 at the piercing aperture.

Figure 6:
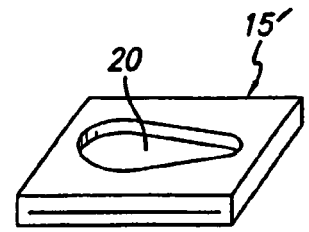
FIG. 6 is a perspective illustration of yet another embodiment of the depth adjustment element of the depth adjustment assembly of the present invention.

Looking specifically to the lancet depth adjustment assembly 10 of the present invention, it includes a depth adjustment element, 15. The depth adjustment element 15 is structured to be positioned in at least partially overlying relation to the piercing aperture 54 of the housing 52, as illustrated in FIG. 1. Along these lines, the depth adjustment element 15 also preferably includes a piercing access 20 defined therein. The piercing access 20 which may be in the form of a series of openings or an elongated slot or gap or opening in the depth adjustment element 15 is preferably structured to permit passage of the piercing tip 56 of the lancet therethrough, generally after it has passed through the piercing aperture 54 of the housing 52. As such, the depth adjustment element 15 is structured and disposed to be at least temporarily and at least partially interposed between a body part of the patient, such as preferably the patient's finger, and the piercing aperture 54. Accordingly, the spacing between the finger and the piercing aperture 54 is defined preferably as a result of a position of the body part of the patient, such as a finger or earlobe, that is permitted by the depth adjustment element 15, and in one embodiment the exterior surface 22 thereof, relative to the piercing aperture 54, and also in the illustrated embodiment, as a result of the thickness of the depth adjustment element 15. For example, in the illustrated embodiments a particular thickness of the depth adjustment element generally at the piercing aperture 54 will correspondingly space the finger from the piercing aperture 54. As a result, a depth to which the piercing tip 56 penetrates the finger is also thereby varied and defined by the depth adjustment element 15. Also from the preceding it follows that the farther away the exterior surface 22 of the depth adjustment element 15 is disposed from the piercing aperture 54, either as a result of a relative positioning of the depth adjustment element 15 and/or a thickness thereof, the greater the spacing between the finger and the piercing aperture 54, and the shorter the depth to which the piercing tip 56 penetrates the finger. As can be appreciated, the piercing tip 56 is generally configured to protrude a predefined, set amount from the piercing aperture 54 of most lancet devices 50, such that varying a position of the finger relative to the lancet device 50 varies the depth to which the piercing tip 56 will penetrate. In yet another embodiment, as illustrated in FIG. 6, the depth adjustment element 15" may include a partially recessed surface and/or a variably sized gap to define the piercing access 20, the dimension and/or configuration thereof defining how close to the piercing aperture 54 the body part to be pierced is able to be positioned. For example, a wide recess or gap allows more of a patient's finger to be disposed within the piercing access 20, thereby reducing the spacing and increasing the penetration depth. Conversely, a tight gap or recess will only allow minimal amounts of the patient's finger to penetrate beyond the exterior surface of the depth adjustment element, thereby increasing the spacing and reducing the penetration depth. Adjustability of this embodiment can be achieved in a similar manner to that described subsequently with regard to the other embodiments.

Figure 2:
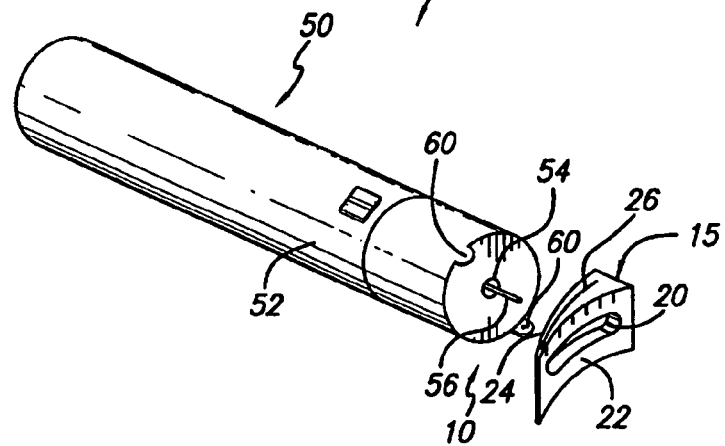
FIG. 2 is a exploded view of a depth adjustment assembly of the present invention in association with a lancet device.
Figure 3:
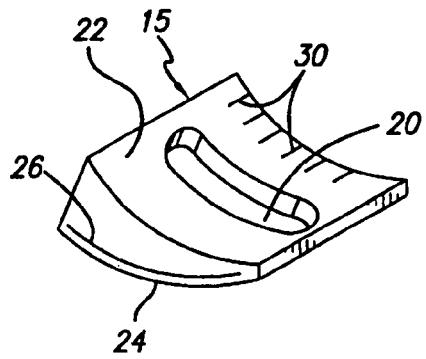
FIG. 3 is a perspective illustration of an embodiment of the depth adjustment element of the depth adjustment assembly of the present invention.
Figure 4:
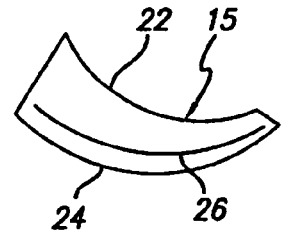
FIG. 4 is a side view of the embodiment of the depth adjustment element of the depth adjustment assembly of the present invention shown in FIG. 3.
Figure 5:
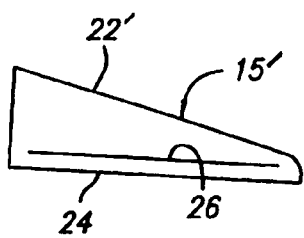
FIG. 5 is a side view of another embodiment of the depth adjustment element of the depth adjustment assembly of the present invention.

Although a plurality of depth adjustment elements 15 may be utilized, each of the depth adjustment elements being removable and having a different structure and/or dimension so as to effectively vary a spacing of the finger from the piercing aperture 54, in the illustrated embodiment, a single depth adjustment element is preferably movably secured to the housing 52 of the lancet device 50. The depth adjustment element 15 is operatively disposed preferably in generally overlying adjustable relation to the piercing aperture 54. For example, as best seen in FIG. 2, although a variety of interlocking structures could be utilized which allow for a generally sliding movement between the depth adjustment element 15 and the housing 52, one embodiment may include the utilization of a guide assembly 60 coupled, either integrally or separately with the housing 52 and structured to movably retain and position the depth adjustment element 15. In the illustrated embodiment the guide assembly 60 includes a pair of upwardly depending members preferably having a pin defined therein. The pin preferably rides within one or more tracks 26, defined in corresponding sides of the depth adjustment element 15. As a result, the guide assembly 60 generally retains the depth adjustment element 15 properly positioned in overlying relation to the piercing aperture 54, however, sliding movement through the tracks 26 permits for corresponding and desired adjustment of the orientation of the depth adjustment element 15. Of course, alternate, more integral and/or captivated configurations wherein sliding movement is still maintained could also be provided. Likewise, a notched, toothed, or other segmented configuration could be provided so as to define set stopping points corresponding to different depths and/or in an embodiment with multiple piercing accesses 20, in aligned relation with a desired piercing access 20.

Figure 7:
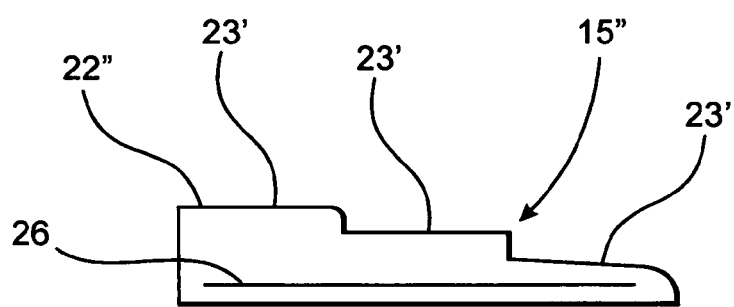
FIG. 7 is a side view of a further embodiment of the depth adjustment element of the depth adjustment assembly of the present invention.

The aforementioned movable and/or sliding positioning between the depth adjustment element 15 and the housing 52 is especially beneficial in the embodiment wherein the depth adjustment element 15 is structured with varying thickness and/or to have an orientation which variably positions the exterior surface 22 of the depth adjustment element 15 at variable distances from the place of the piercing aperture 54. For example, although not illustrated for clarity, a uniformly dimensioned depth adjustment element 15 may be provided, with the one or more tracks 26, being oriented so as to selectively space the depth adjustment element 15 from the piercing aperture 54, thereby correspondingly spacing the exterior surface 22 and a finger disposed thereon. In the illustrated embodiment, however, the depth adjustment element 15 preferably includes a gradual variance in thickness, such as a taper and/or wedge and/or stepped shaped configuration. As a result, sliding adjustment of the depth adjustment element 15, 15', 15" relative to the piercing aperture 54 effectively varies the position of the exterior surface 22, 22', 22" of the depth adjustment element 15, 15', 15" in turn varying a positioning and spacing of the finger relative to the piercing tip 56 at its piercing orientation. As seen in the embodiment of FIG. 7, two or more, but preferably three different piercing locations are provided, on at each step 23'. Of course, each step 23' can also vary in thickness. Furthermore, if desired, indicia 30 may be effectively positioned on the depth adjustment element 15, 15', 15" so as to effectively indicate the depth to which the piercing tip 56 would penetrate the finger in accordance with the portion of the depth adjustment element 15, 15', 15" which is overlying the piercing aperture 54 in a particular position and/or orientation.

As can be appreciated, the exterior surface 22 is structured to generally confront and engage the finger, while the interior surface 24 of the depth adjustment element 15 generally confronts the piercing aperture 54. As such, if desired, a generally symmetrical rounded configuration could be provided for the depth adjustment element. Alternatively, as illustrated, the exterior surface 22 and the interior surface 24 may be configured such that a spacing therebetween and a relative curvature actually varies along a length of the depth adjustment element 15. As a result, a generally continuous and uniform engagement between the interior surface 24 of the depth adjustment element 15 is maintained with the housing 52, achieving a general uniformity and stability, while the position of the overlying portion of the exterior surface 22 varies to effectively determine the spacing of the finger disposed thereon.

As can be appreciated, the exterior surface 22 is structured to generally confront an engage the finger, while the interior surface 24 of the depth adjustment element 15 generally confronts the piercing aperture 54. As such, if desired, a generally symmetrical rounded configuration could be provided for the depth adjustment element. Alternatively, as illustrated, the exterior surface 22 and the interior surface 24 may be configured such that a spacing therebetween and a relative curvature actually varies along a length of the depth adjustment element 15. As a result, a generally continuous and uniform engagement between the interior surface 24 of the depth adjustment element 15 is maintained with the housing 52, achieving a general uniformity and stability, while the position of the overlying portion of the exterior surface 22 varies to effectively determine the spacing of the finger disposed thereon.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. For use in combination with a lancet device including a lancet disposed within a housing and structured to move into a piercing orientation wherein a piercing tip of the lancet protrudes from a piercing aperture defined in the housing, a lancet depth adjustment assembly comprising:

a depth adjustment element, said depth adjustment element secured in at least partially overlying relation to a piercing aperture of a housing;

said depth adjustment element including a piercing access, said piercing access including at least one opening structured to permit passage of a piercing tip of a lancet therethrough;

said depth adjustment element structured and disposed to be at least temporarily and at least partially interposed between a finger and the piercing aperture so as to define a spacing between the finger and the piercing aperture, and accordingly a depth to which the piercing tip penetrates the finger;

said depth adjustment element having an interior surface and an exterior surface disposed in at least partially overlying relation to the piercing aperture of the housing, said exterior surface comprising a stepped configuration including a plurality of steps disposed in an exteriorly exposed location on said adjustment element, each of said plurality of steps disposed at a different spacing from the piercing aperture and structured to independently engage and maintain the finger at a corresponding one of said different spacings from the piercing aperture, and said piercing access extending at least partially along a length of said depth adjustment element so as to permit the passage of the piercing tip therethrough when said depth adjustment element is disposed in overlying relation to the piercing aperture in at least two distinct piercing locations.

2. A lancet depth adjustment assembly as recited in claim 1 wherein said depth adjustment element is movably secured to the housing and is structured to vary a portion of said depth adjustment element which generally overlies the piercing aperture.

3. A lancet depth adjustment assembly as recited in claim 1 further comprising a guide assembly coupled to the housing and structured to movably retain and position said depth adjustment element relative to the housing.

4. A lancet depth adjustment assembly as recited in claim 1 wherein said depth adjustment element includes indicia disposed thereon to indicate the depth to which the piercing tip penetrates the finger in accordance with said portion of said depth adjustment element which generally overlies the piercing aperture.

5. A lancet depth adjustment assembly as recited in claim 1 wherein said depth adjustment element includes an at least partially tapered configuration and is movably secured over the piercing aperture so as to vary said spacing between the finger and the piercing aperture in response to which of said plurality of steps is disposed in overlying relation to the piercing aperture.

6. A lancet depth adjustment assembly as recited in claim 1 wherein said depth adjustment element includes an at least partially wedge shaped configuration structured to selectively maintain said spacing between the finger and the piercing aperture.

7. A lancet depth adjustment assembly as recited in claim 1 wherein, said interior surface is disposed in generally confronting relation to the housing.

8. For use in combination with a lancet device including a lancet disposed within a housing and structured to move into a piercing orientation wherein a piercing tip of the lancet protrudes from a piercing aperture defined in the housing, a lancet depth adjustment assembly comprising:

a depth adjustment element, said depth adjustment element adjustably secured in at least partially overlying relation to a piercing aperture of a housing;

said depth adjustment element including a piercing access structured to permit passage of a piercing tip of a lancet therethrough;

said depth adjustment element structured and disposed to be at least temporarily and at least partially interposed between a finger and the piercing aperture so as to define a spacing between the finger and the piercing aperture, and accordingly a depth to which the piercing tip penetrates the finger;

said depth adjustment element having an interior surface and an exterior surface, said exterior surface comprising a stepped configuration including a plurality of steps, each of said plurality of steps disposed in an exteriorly exposed location on said adjustment element at a different spacing from the piercing aperture, and each of said plurality of steps structured to independently engage and maintain the finger at a corresponding one of said different spacings from the piercing aperture.

9. A lancet device comprising:

a lancet disposed within a housing and being structured to move into a piercing orientation, wherein a piercing tip of the lancet protrudes from a piercing aperture each time the lancet device is used;

a depth adjustment element having an interior surface and an exterior surface, wherein the interior and exterior surfaces are positioned in at least partially overlying relation to the piercing aperture of the housing, said exterior surface comprising a stepped configuration including a plurality of steps disposed in an exteriorly exposed location on said adjustment element, each of said plurality of steps disposed at a different spacing from the piercing aperture and structured to independently engage and maintain the finger at a corresponding one of said different spacings from the piercing aperture, and wherein a position of each of said plurality of steps is adjustable relative to the piercing aperture.

10. The lancet device of claim 9, wherein the piercing tip of the lancet protrudes from the piercing aperture by a predetermined uniform amount each time the lancet device is used, each of said different spacings between the piercing aperture and corresponding ones of said plurality of steps is dimensioned to establish a different depth to which the piercing tip penetrates the finger.

11. The lancet device of claim 9, wherein, when the depth adjustment element is located in one position relative to the piercing aperture, the depth to which the piercing tip penetrates a user's finger is different than when the depth adjustment element is located in another position.

12. The lancet device of claim 9, wherein said depth adjustment element is a single adjustable depth adjustment element.

13. The lancet device of claim 9, further comprising a guide assembly structured to movably retain and position said depth adjustment element in overlying relation to the piercing aperture.

14. The lancet device of claim 9, wherein each of said plurality of steps is disposed and structured to effectively and independently receive and retain a user's finger seated therein thereby operably aligning the finger and prevent the finger from shifting.

15. A lancet device comprising:

a lancet disposed within a housing and being structured to move into a piercing orientation wherein a piercing tip of the lancet protrudes from a piercing aperture by a predetermined uniform amount each time the lancet device is used;

a depth adjustment element having an interior surface and an exterior surface, wherein the interior and exterior surfaces are positioned in at least partially overlying relation to the piercing aperture of the housing, said exterior surface comprising a stepped configuration including a plurality of steps disposed in an exteriorly exposed location on said adjustment element, each of said plurality of steps defining a different spacing between a finger and a piercing aperture, and accordingly a varying depth to which the piercing tip penetrates the finger, wherein a position of said plurality of steps is collectively adjustable relative to the piercing aperture; and a guide assembly structured to movably retain and position said depth adjustment element in overlying relation to the piercing aperture.

* * * * *